(12) United States Patent
Keller, Jr. et al.

(10) Patent No.: US 7,722,807 B2
(45) Date of Patent: May 25, 2010

(54) DEVICE AND CONTAINERS FOR EMITTING VOLATILE COMPOSITIONS

(75) Inventors: Leonard Joseph Keller, Jr., Cincinnati, OH (US); Michael Sean Farrell, Terrace Park, OH (US); Gary Jay Groznik, Liberty Township, OH (US); Dean Robert McCoy, Burlington, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 1143 days.

(21) Appl. No.: 11/216,618

(22) Filed: Aug. 31, 2005

(65) Prior Publication Data

US 2007/0048173 A1 Mar. 1, 2007

Related U.S. Application Data

(60) Provisional application No. 60/605,774, filed on Aug. 31, 2004.

(51) Int. Cl.
| | |
|---|---|
| *A61L 9/00* | (2006.01) |
| *A62B 7/08* | (2006.01) |
| *F24F 6/08* | (2006.01) |
| *A61H 33/12* | (2006.01) |
| *A01K 63/06* | (2006.01) |
| *B65D 65/00* | (2006.01) |
| *B65D 21/00* | (2006.01) |
| *A24F 25/00* | (2006.01) |
| *B05B 9/00* | (2006.01) |
| *A62C 13/62* | (2006.01) |

(52) U.S. Cl. .................. 422/5; 422/1; 422/28; 422/120; 422/123; 422/124; 422/125; 422/126; 422/305; 422/306; 392/392; 392/395; 392/403; 392/386; 392/445; 206/432; 215/10; 239/34; 239/44; 239/149; 239/303

(58) Field of Classification Search ..................... 422/1, 422/5, 28, 120, 123–126, 305, 306; 392/392, 392/395, 403, 386, 445; 206/432; 215/10; 239/34, 44, 149, 303
See application file for complete search history.

(56) References Cited

U.S. PATENT DOCUMENTS 4,196,808 A 4/1980 Pardo (Continued)

FOREIGN PATENT DOCUMENTS

JP U-S64-39745 9/1987

(Continued)

*Primary Examiner*—Jill Warden
*Assistant Examiner*—Monzer R. Chorbaji
(74) *Attorney, Agent, or Firm*—Thihault Fayette; Larry L. Huston; Amy I. Ahn-Roll

(57) ABSTRACT

The invention is directed to devices and containers for emitting volatile compositions.

In one embodiment, the invention is directed to a device that includes a holding mechanism for substantially concurrently and releasably retaining two containers.

In one embodiment, the invention is directed to a first container having a first volatile composition and a second container having a second volatile composition where the first and the second containers are operably connected to each other to form a cartridge.

In one embodiment, the invention is directed to a method of emitting a first and a second volatile composition.

22 Claims, 15 Drawing Sheets

U.S. PATENT DOCUMENTS

| | | | |
|---|---|---|---|
| 5,158,191 A * | 10/1992 | Douglas et al. | 215/10 |
| 5,316,159 A | 5/1994 | Douglas et al. | |
| 6,656,438 B1 | 12/2003 | Kinoshita et al. | |
| 2002/0146242 A1 * | 10/2002 | Vieira | 392/395 |
| 2002/0158351 A1 | 10/2002 | Wohrle | |
| 2002/0159916 A1 | 10/2002 | Whitby et al. | |
| 2004/0247301 A1 | 12/2004 | Yip et al. | |

FOREIGN PATENT DOCUMENTS

| | | |
|---|---|---|
| JP | U-H04-065550 | 10/1990 |
| JP | U-HO4-111351 | 9/1992 |
| JP | A-2002-065382 | 3/2002 |

* cited by examiner

DEVICE AND CONTAINERS FOR EMITTING VOLATILE COMPOSITIONS

FIELD OF THE INVENTION

In one embodiment, the invention relates to a mechanism for connecting containers to a device for emitting volatile compositions.

In another embodiment, the invention relates to a container(s) having a volatile composition for use with a device for emitting volatile compositions.

In another embodiment, the invention relates to methods for emitting a volatile composition.

BACKGROUND OF THE INVENTION

It is generally known to use an electrical device to evaporate a perfume and/or fragrance composition into a space, particularly a domestic space, e.g., a living room, to provide a pleasant aroma. There are a variety of such devices on sale, for example the AIRWICK® Diffuser ACTIF® (manufactured by Reckitt Benckiser) or the AMBI-PUR® fragrance diffuser (manufactured by Sara Lee). Generally, these devices include an electrical heating element for evaporating a perfume or fragrance composition which is stored in a container. Typically, the container is either threadably connected or clipped to the device during use.

It has been observed that a person using this type of device can quickly become accustomed to the perfume or fragrance and, after a while, he or she will not perceive the fragrance strength as being as intense and may not notice it at all. This is a well-known phenomenon called habituation. A solution to this problem is proposed in copending U.S. patent application Ser. No. 10/417,462 and Ser. No. 10/417,456 both to Kvietok et al, filed Apr. 16, 2003, in U.S. provisional patent applications Ser. No. 60/507,772 and 60/507,807 to Kievtok et al., both filed Oct. 1, 2003 and in U.S. patent application Ser. No. 10/820,284 to Woo et al., filed Apr. 8, 2004, all assigned to The Procter & Gamble Company. Kvietok et al. discloses method and devices for emitting volatile compositions. One example emitting device of Kvietok et al. uses a first heating element and a second heating element for heating corresponding first and second wicks which are respectively in communication with a first and a second volatile composition. The device of Kvietok et al. allows the first and second volatile compositions to be vaporized in various sequences, either random or non-random.

The inventors have observed that the positioning of the first and second wicks relative to the first and second heating elements has an impact on the volatilization rate of the respective volatile compositions. For example, if the first wick is not properly positioned relative to the first heating element, the volatilization rate of the first volatile composition can either increase or decrease. This unwanted higher or lower volatilization rate of a first volatile composition relative to the volatilization rate of a second volatile composition can result in a partial loss of the desired effect of a first volatile composition. In addition, due to this unwanted higher or lower volatilization rate of the first volatile composition, over time, the first or second volatile composition can be totally vaporized while a significant amount of the other composition is still left in the container. Although a similar problem can exist with emitting devices capable of continuously vaporizing a single volatile composition if the single wick is not properly positioned, it can either stay unnoticed or can be easily compensated by decreasing or increasing the amount of heat applied to this single wick.

The inventors have found that with emitting devices capable of vaporizing at least two volatile compositions via at least two separate wicks, it is desirable that the volatilization rate of each volatile compositions be controlled.

The inventors have found that it is possible to remediate to this problem via the attachment mechanism used to connect the container(s) to the emitting device.

It is therefore an object of the invention to provide a suitable mechanism for releasably connecting containers to a device for emitting volatile compositions.

It is also an object of the invention to provide containers having at least a first and a second volatile composition which are operably connectable to an emitting device.

It is another object of the invention to provide a method for emitting a first and a second volatile composition with an emitting device.

SUMMARY OF THE INVENTION

In one embodiment, the invention is directed to a device for emitting at least two volatile compositions, the device comprising an vaporizing unit having a first heating element, at least a second heating element, and a holding mechanism for substantially concurrently and releasably retaining a first and at least a second container, a first container having a first volatile composition and a second container having a second volatile composition wherein the first and second containers are releasably connected to the vaporizing unit by the holding mechanism.

In another embodiment, the invention is directed to a cartridge for a device for emitting at least a first and a second volatile composition, the cartridge comprising a first container defining a first volume and comprising a first wick in communication with the first volume, the first wick extending at least partially through an opening of the first container wherein the first container comprises a first volatile composition and at least a second container defining a second volume and comprising a second wick in communication with the second volume, the second wick extending at least partially through an opening of the second container wherein the second container comprises a second volatile composition and wherein the first container is operably connected to the second container independently of the device such that the first wick is fixedly located relative to the second wick.

In another embodiment, the invention is directed to a method of emitting a first and at least a second volatile composition with an vaporizing unit capable of vaporizing a first and at least a second volatile composition, the method comprising providing a first container comprising a first volatile composition, providing a second container comprising a second volatile composition, operably and substantially concurrently connecting said first and second containers to said vaporizing unit and actuating said vaporizing unit.

In another embodiment, the invention is directed to a cartridge for an vaporizing unit capable of emitting a first and at least a second volatile composition, the cartridge comprising a container having at least one outer wall and at least one inner wall defining a first volume and at least a second volume wherein the first and second volumes are separated by the inner wall, a first volatile composition stored in the first volume, at least a second volatile composition stored in the second volume, a first wick in communication with the first volatile composition and extending at least partially outside of the first volume and a second wick in communication with the second volatile composition and extending at least partially outside of the second volume.

In another embodiment, the invention is directed to a cartridge for a vaporizing unit capable of emitting a first and at least a second volatile composition, said cartridge comprising a retaining member having at least a first opening for receiving at least a portion of a first container and a first clip member extending from a top surface of the retaining member and a first container comprising a volatile composition, the first container extending at least partially through the first opening of the retaining member.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

Figure 1:
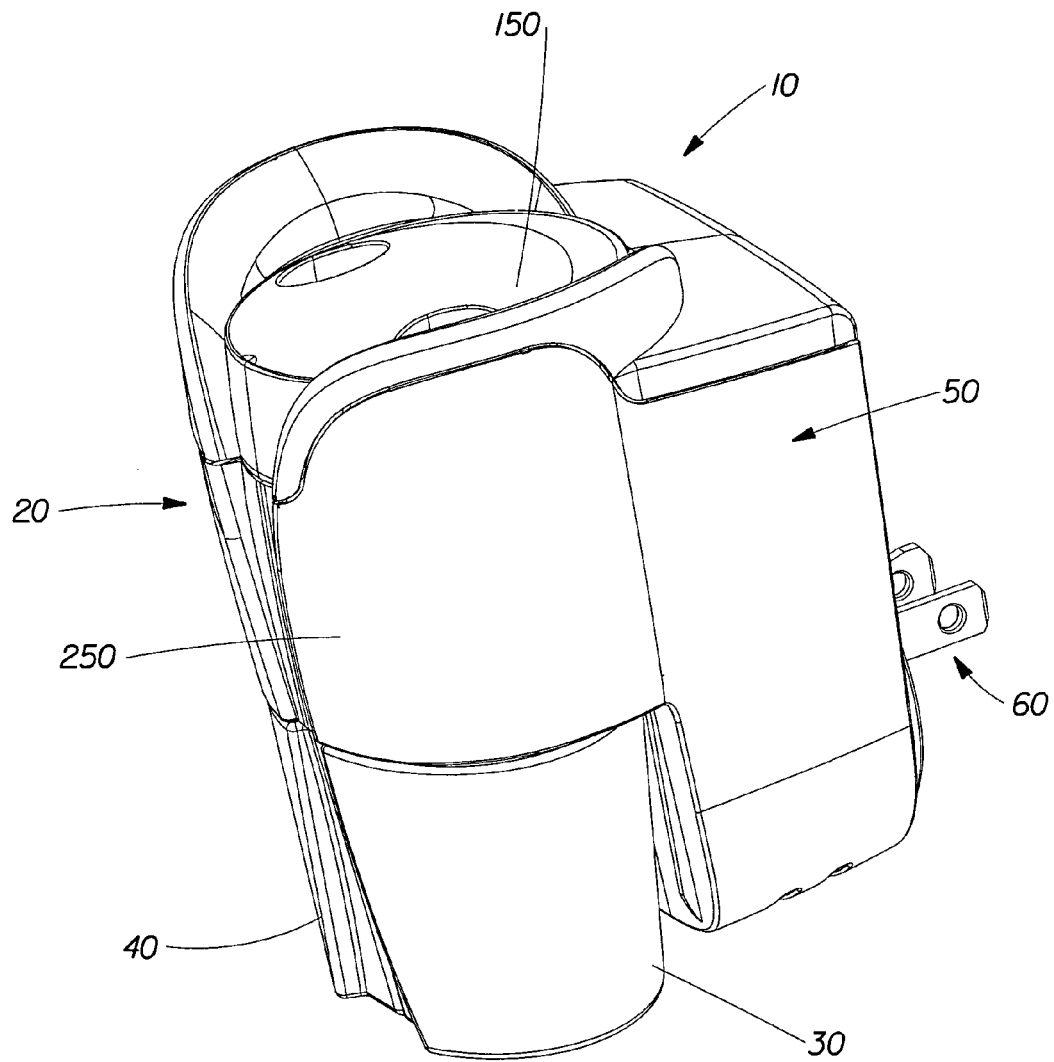
FIG. 1 is a perspective view of a device for emitting volatile compositions according to one embodiment of the invention.

All documents cited herein are, in relevant part, incorporated herein by reference; the citation of any document is not to be construed as an admission that it is prior art with respect to the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All parts, ratios, and percentages herein, in the Specification, Examples, and Claims, are by weight unless otherwise stated and all numerical limits are used with the normal degree of accuracy afforded by the art, unless otherwise specified.

While not intending to limit the utility of the vaporizing device herein, it is believed that a brief description of its use in association with containers will help elucidate the invention.

Numerous devices are known to emit a volatile composition such as a perfume or fragrance. The most common include an vaporizing unit and a container connectable to the vaporizing unit. The vaporizing unit typically includes a heating element electrically connected to an electric plug which is itself connectable to an electrical outlet. The container is typically filled with a volatile perfume, and includes a wick dipped into the perfume and extending from an opening of the container. When the container is connected to the vaporizing unit, a portion of the wick extending from the container is located in the vicinity of the heating element which vaporizes the perfume into a room.

It has been observed that a person using this type of device can quickly become accustomed to the perfume or fragrance and, after a while, he or she will not perceive the fragrance strength as being as intense and may not notice it at all. This is a well-known phenomenon called habituation. A solution to this problem is proposed in copending U.S. patent application Ser. No. 10/417,462 and Ser. No. 10/417,456 both to Kvietok et al, filed Apr. 16, 2003, in U.S. provisional patent applications Ser. No. 60/507,772 and 60/507,807 to Kievtok et al., both filed Oct. 1, 2003 and in U.S. patent application Ser. No. 10/820,284 to Woo et al., filed Apr. 8, 2004, all assigned to The Procter & Gamble Company. Kvietok et al. discloses method and devices for emitting volatile compositions. One example emitting device of Kvietok et al. uses a first heating element and a second heating element for heating corresponding first and second wicks which are respectively in communication with a first and a second volatile composition. The device of Kvietok et al. allows the first and second volatile compositions to be vaporized in various sequences, either random or non-random.

The inventors have observed that the positioning of the first and second wicks relative to the first and second heating elements has an impact on the volatilization rate of the respective volatile compositions. For example, if the first wick is not properly positioned relative to the first heating element, the volatilization rate of the first volatile composition can either increase or decrease. This unwanted lower volatilization rate of a first volatile composition relative to the volatilization rate of a second volatile composition can result in a partial loss of the desired effect of a first volatile composition. In addition, due to this unwanted lower volatilization rate of the first volatile composition, over time, the second volatile composition can be totally vaporized while a significant amount of the first composition is still left in the container. Although a similar problem can exist with emitting devices capable of continuously vaporizing a single volatile composition, it can either stay unnoticed or can be easily compensated by increasing the amount of heat applied to the single wick.

The inventors have found that with emitting devices capable of vaporizing at least two volatile compositions via at least two separate wicks, it is desirable that the volatilization rate of each volatile compositions be controlled.

The foregoing considerations are addressed by the present invention, as will be clear from the detailed disclosures which follow.

As discussed more fully hereafter, the present invention is, in its most preferred form, directed to a mechanism for releasably connecting containers to a device for emitting volatile compositions stored in the containers, as well as, the containers for storing the volatile compositions.

Reference will now be made in detail to the present preferred embodiments of the invention, examples of which are illustrated in the accompanying drawings wherein like numerals indicate the same elements throughout the views and wherein reference numerals having the same last two digits (e.g., 20 and 120) connote similar elements.

FIG. 1 shows a perspective view of a device 10 for emitting at least two volatile compositions. In one embodiment, the device 10 includes an vaporizing unit 20, a first container 30 for storing a first volatile composition and a second container 40 for storing a second volatile composition.

In one embodiment, the vaporizing unit 20 comprises a housing 50 having a top portion 150 and a bottom portion 250, and electrical plugs 60 for electrically connecting the vaporizing unit to an electrical outlet as it is well-known in the art.

In one embodiment, the bottom portion 250 of the housing 50 forms a semi-enclosed cavity for receiving at least a portion, preferably the top portion, of the first and second containers 30 and 40 which can be inserted within the semi-enclosed cavity via a lower opening of the semi-enclosed cavity.

I. Vaporizing Unit

Figure 2:
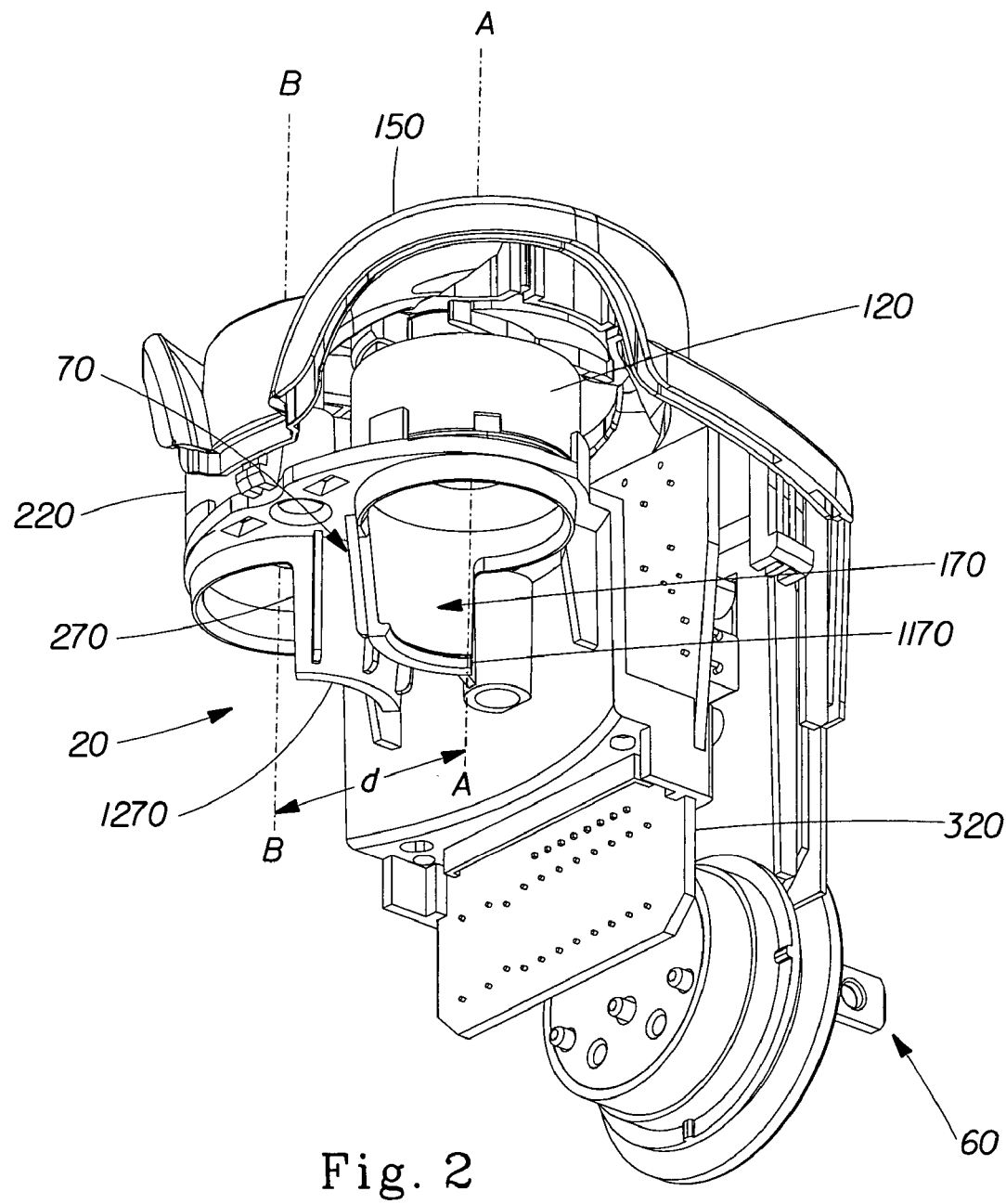
FIG. 2 is a perspective view of the vaporizing unit of FIG. 1 where a portion of the housing has been removed for clarity.

FIG. 2 shows a perspective view of the vaporizing unit 20 where the bottom portion 250 of the housing 50 and the first and second containers 30 and 40 are not shown for clarity.

The vaporizing unit 20 includes a first heating element 120 and at least a second heating element 220 for respectively vaporizing the first and second volatile compositions.

In one embodiment, the heating elements 120 and 220 are operably and electrically connected to the electric plugs 60. One skilled in the art will understand that alternatively, the heating elements 120 and 220 can be connected to a battery rather than electric plugs and still provide the same benefits. In a preferred embodiment, the heating elements 120 and 220 are operably and electrically connected to a switching mechanism 320 via electrical wires (not shown) in order to vaporize the first and second volatile compositions sequentially. A non-limiting example of a suitable switching mechanism is described in copending U.S. patent application Ser. No. 10/417,462 and Ser. No. 10/417,456 both to Kvietok et al, filed Apr. 16, 2003, and assigned to The Procter & Gamble Company.

In one embodiment, the heating elements 120 and 220 can be in the form of annular rings having an inner surface and an outer surface, such that at least a portion of the inner surface of the heating elements is capable of providing heat to a wick positioned in the vicinity of the inner surface of the heating elements. One skilled in the art will understand that the heating elements can have other shapes and still provide at least some of the same benefits.

In one embodiment, the heating elements 120 and 220 are located within the lower housing such that they are each positioned between the upper housing 150 and the semi-enclosed cavity formed by the lower housing.

In one embodiment, the first heating element 120 has an axis of symmetry A-A and the second heating element 220 has an axis of symmetry B-B. In a preferred embodiment, the first and second heating elements 120 and 220 are positioned within the lower housing such that the axis A-A is substantially parallel to the axis B-B. In an even preferred embodiment, the first heating element 120 and the second heating element 220 are positioned within the lower housing at substantially the same height relative to the semi-enclosed cavity formed by the lower housing.

In one embodiment, the distance d between the axis A-A and the axis B-B is between about 3 mm and about 200 mm, preferably between about 10 mm and about 50 mm, more preferably between about 25 mm and about 35 mm.

In one embodiment, the vaporizing unit 20 includes a holding mechanism 70 for substantially concurrently and releasably connecting the first and second containers 30 and 40 to the vaporizing unit. By "substantially concurrently connecting the first and second containers to the vaporizing unit", it is meant that one container cannot be connected to the unit without the other(s) container being also connected to the unit. In one embodiment, the holding mechanism 70 is located at least partially within the semi-enclosed cavity formed by the lower housing. In one embodiment the holding mechanism 70 is located between the first heating element 120 and the second heating element 220.

Figure 3:
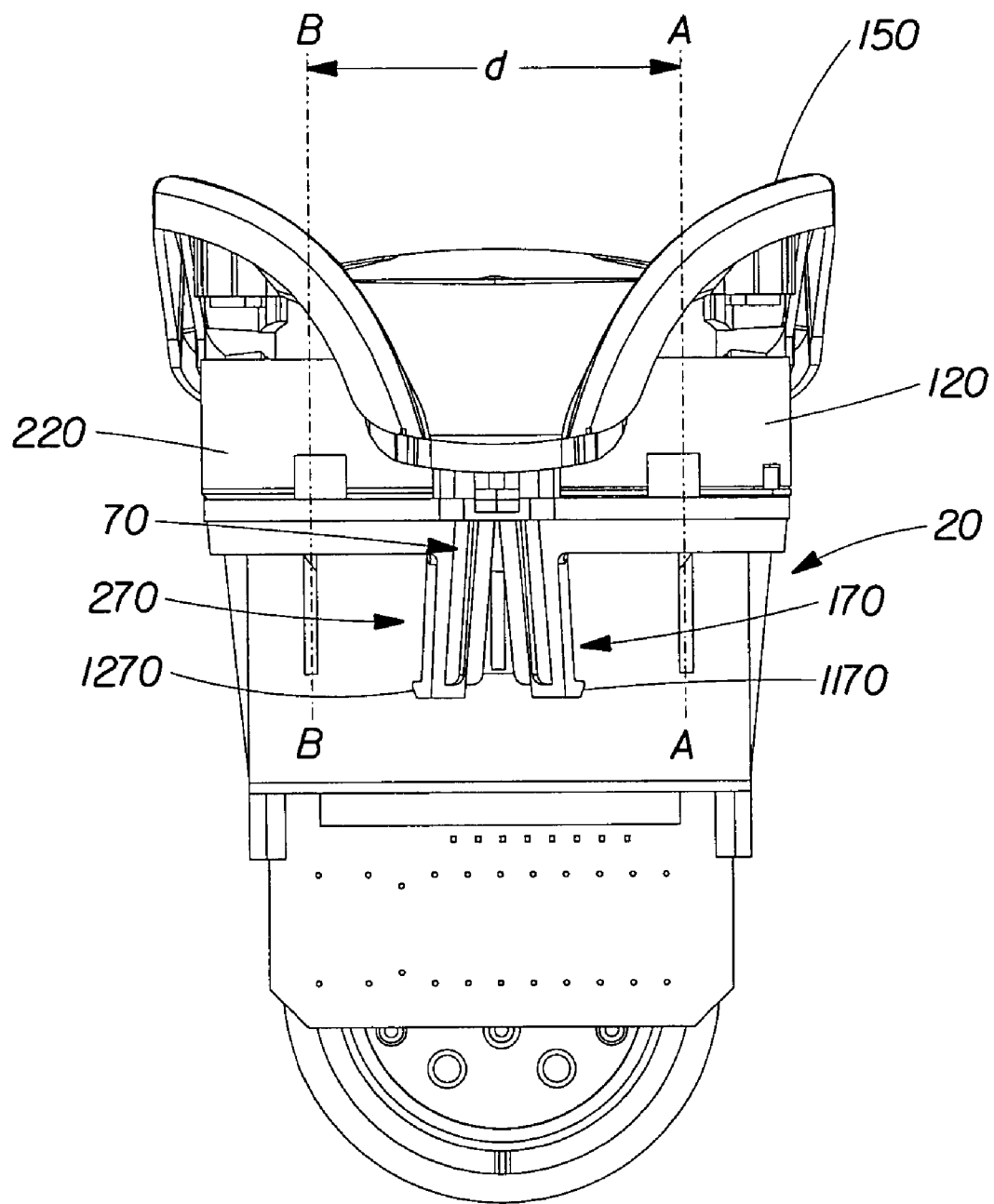
FIG. 3 is a front view of the vaporizing unit of FIG. 2.

In one embodiment, the holding mechanism includes a first clip member 170 and a second clip member 270 extending substantially downwardly and at least partially within the semi-enclosed cavity formed by the lower housing. In one embodiment, the first clip member 170 comprises a protrusion or lip 1170 and the second clip member 270 comprises a protrusion or lip 1270. In a preferred embodiment, the protrusions 1170 and 1270 protrude substantially outwardly and towards opposite directions as shown in FIG. 3.

In one embodiment, at least one of the first and second clip members 170 and 270, but preferably both clip members are flexible such that the lower portion of at least the first clip member 170 (but preferably the lower portion of both the first and second clip members 170 and 270) is moveable inwardly when subjected to a force and returns to its original position when this force ceases to be applied. In a preferred embodiment, the protrusions 1170 and 1270 have an arcuate shape.

II. Container(s)

As previously discussed, the device for emitting at least two volatile compositions includes a first container 30 for storing a first volatile composition and a second container 40 for storing a second volatile composition.

Figure 4:
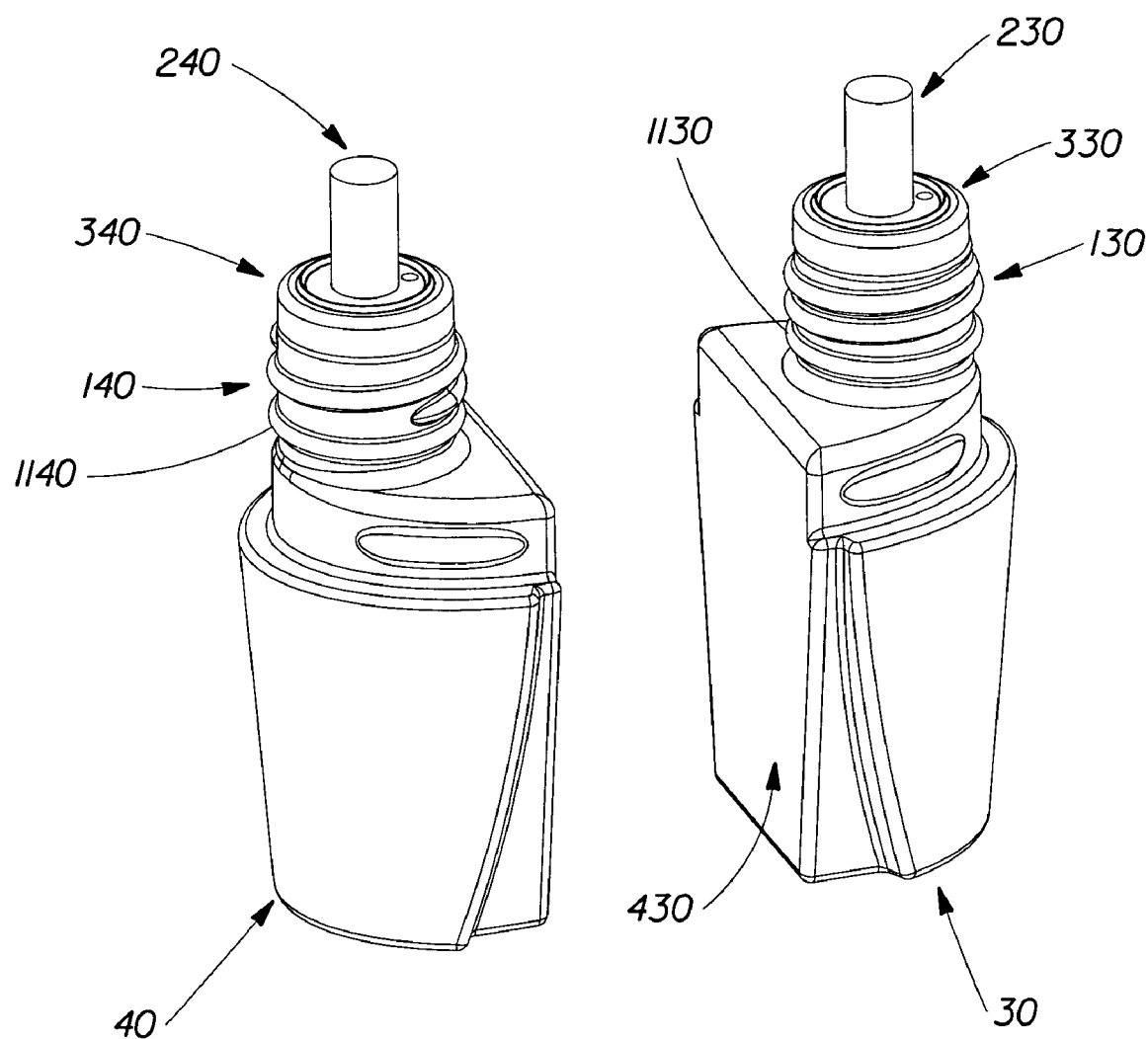
FIG. 4 is a perspective view of a first and a second container according to one embodiment of the invention.

In one embodiment shown in FIG. 4, the first container 30 includes a neck 130 preferably extending from the top portion of the container 30, a wick 230 that is dipped into the first volatile composition stored in the container 30 and which extends at least partially from the neck 130 of the container and a plug member 330 for centering the wick 230 relative to the opening of the neck 130 and for preventing the first volatile composition from leaking out off the container 30.

In one embodiment, the neck 130 includes a projection 1130 for engaging one of the protrusions 1170 or 1270 of the holding mechanism 70. In a preferred embodiment, the projection 1130 is a ring projecting radially and outwardly from the neck 130.

In one embodiment, the first container 30 has at least one side 430 which can be placed substantially in facial relationship with a corresponding side of at least a second container 40. One skilled in the art will understand that in order to maximize the volume available to store a first and a second volatile composition, it is beneficial to position a first and a second container in facial relationship. In a preferred embodiment, the side 430 is substantially flat.

In one embodiment, the second container 40 includes a neck 140, preferably extending from the top portion of the container 40, a wick 240 that is dipped into the second volatile composition stored in the container 40 and which extends at least partially from the neck 140 of the container 40 and a plug member 340 for centering the wick 240 relative to the opening of the neck 140 and for preventing the second volatile composition from leaking out off the container 40. In one embodiment, the neck 140 includes a projection 1140 for engaging the corresponding protrusions 1270 or 1170 of the holding mechanism 70. In a preferred embodiment, the projection 1140 is a ring projecting radially and outwardly from the neck 140.

Figure 5:
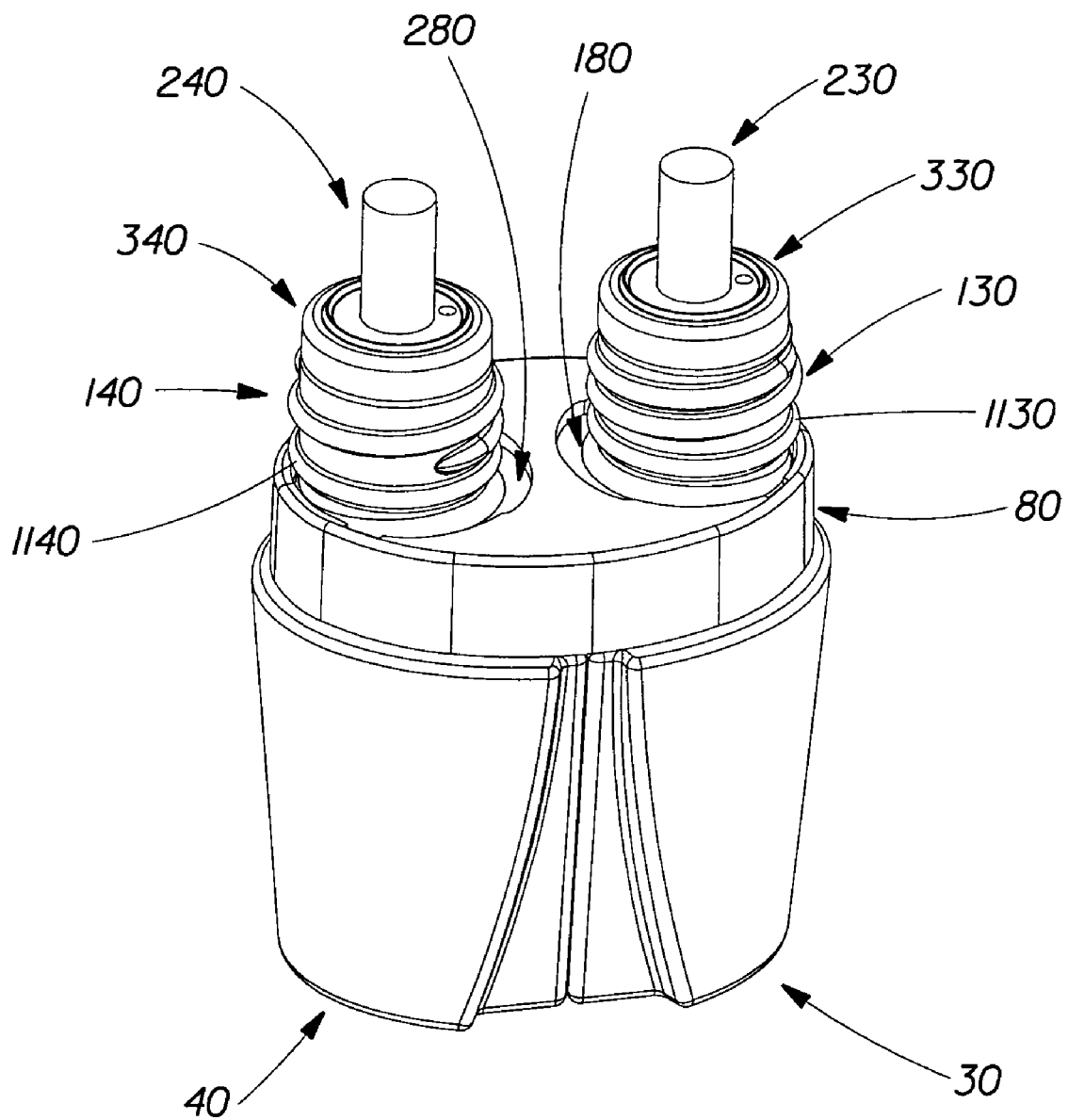
FIG. 5 is a perspective view of a cartridge according to one embodiment of the invention.

In one embodiment shown in FIG. 5, a first container 30 as previously described is operably connected to a second container 40 to form a cartridge for the vaporizing unit previously discussed. In a preferred embodiment, the first and second containers 30 and 40 are operably connected to each other independently from the vaporizing unit.

In one embodiment, the first and second containers 30 and 40 are operably connected such that the first wick 130 is substantially parallel to the axis A-A of the first heating element 120 and the second wick 140 is substantially parallel to the axis B-B of the second heating element 220 when the first and second containers 30 and 40 are connected to the vaporizing unit 20. In a preferred embodiment, the first and second containers 30 and 40 are operably connected such that the distance between the center of the first wick 130 and the second wick 140 is substantially equal to the distance d between the axis A-A of the first heating element 120 and the axis B-B of the second heating element 220.

The first and second containers can be operably connected via any suitable mechanism known in the art.

In one embodiment shown in FIG. 5, the first container and the second container are operably connected by a retaining member 80 having a first opening 180 which is engageable by the first neck 130 and a second opening 280 which is engageable by the second neck 140 and which can be permanently or releasably clipped or snapped onto portions of both the first and second containers. When the retaining member 80 is clipped or snapped onto the first and second containers, the position and distance between the first and second wicks 130, 140 is substantially fixed.

Figure 6:
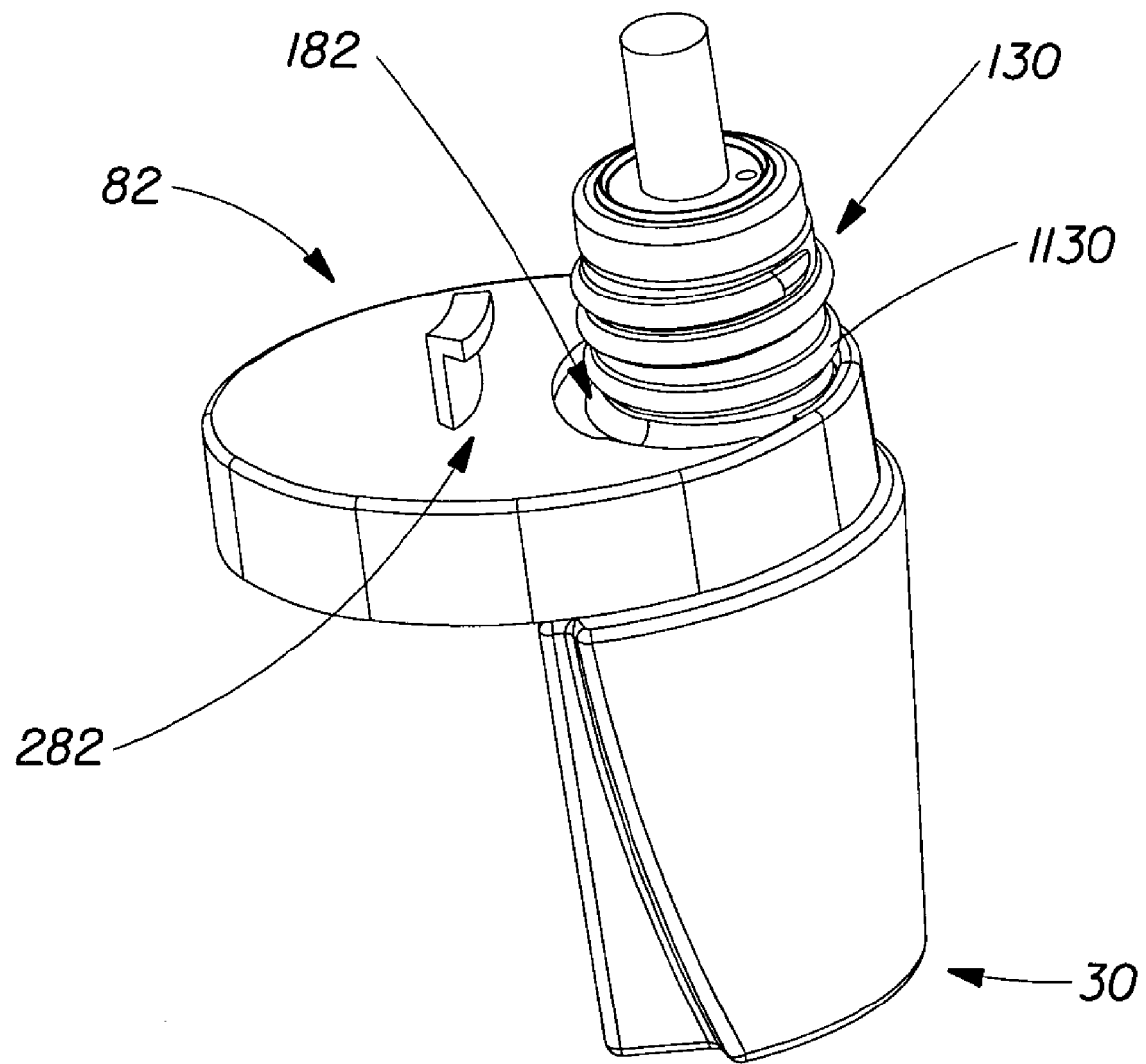
FIG. 6 is a perspective view of a cartridge according to another embodiment of the invention.

In one embodiment shown in FIG. 6, a first container 30 can be operably connected to a retaining member 82 having an opening 182 which can be engaged by the neck 130 of the container 30 and having a clip element 282 for engaging either the first or second clip members 170, 270 of a holding mechanism 70. One skilled in the art will understand that in this embodiment, the clip element 282 and the projection 1130 of the container 30 allow the container to be releasably connected to a vaporizing unit having the holding mechanism previously described. Among other benefits, the retaining member 82 allows a consumer to use the vaporizing unit 20 with a single container if he or she so desires.

Figure 7:
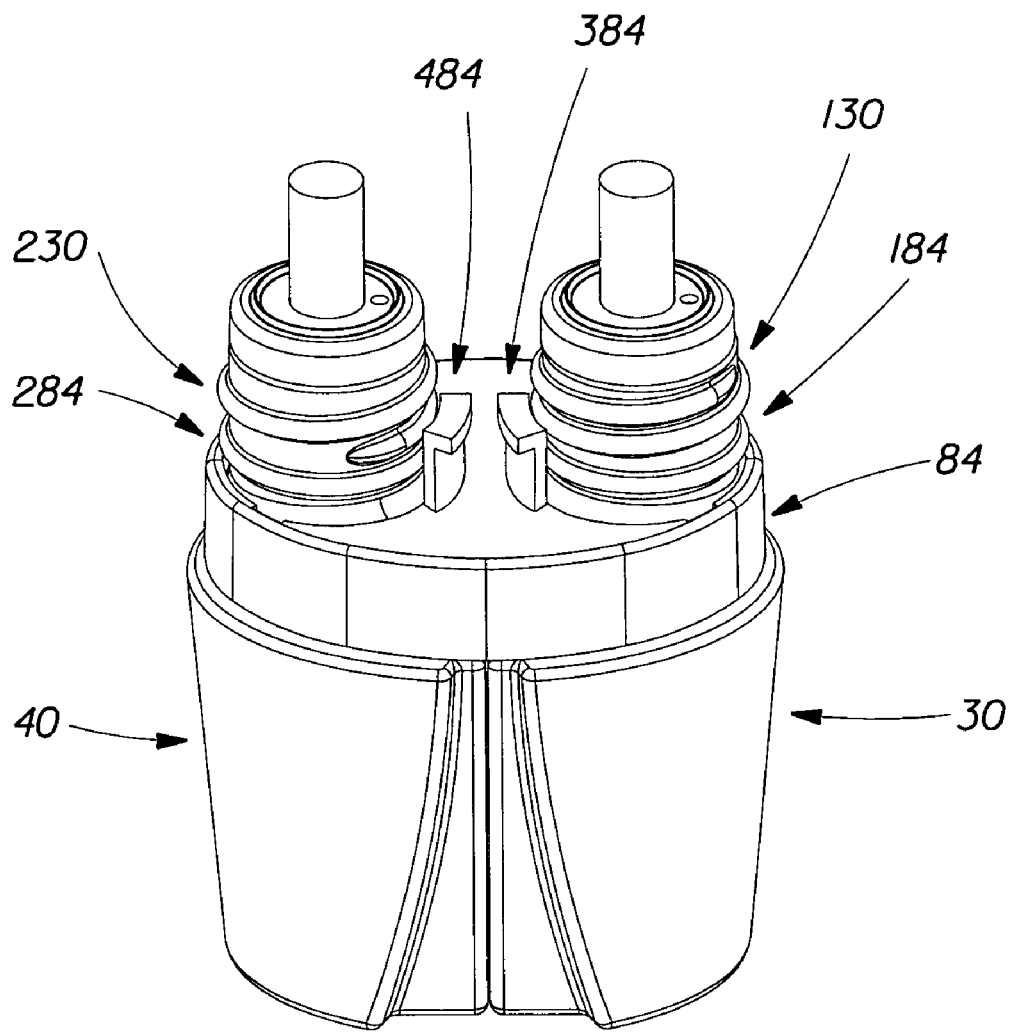
FIG. 7 is a perspective view of a cartridge according to another embodiment of the invention.

In one embodiment shown in FIG. 7, a first container 30 and at least a second container 40 can be operably connected to a retaining member 84 having an opening 184 which can be engaged by the neck 130 of the container 30 and a second opening 284 which can be engaged by the neck 140 of the second containers 40. In one embodiment, the retaining member 84 includes a first clip element 384 and a second clip element 484 for respectively engaging either the first or second clip members 170, 270 of a holding mechanism 70. One skilled in the art will understand that in this embodiment, the retaining member 84 allows a user to connect containers, which do not include the projections previously discussed, to a vaporizing unit.

Figure 8:
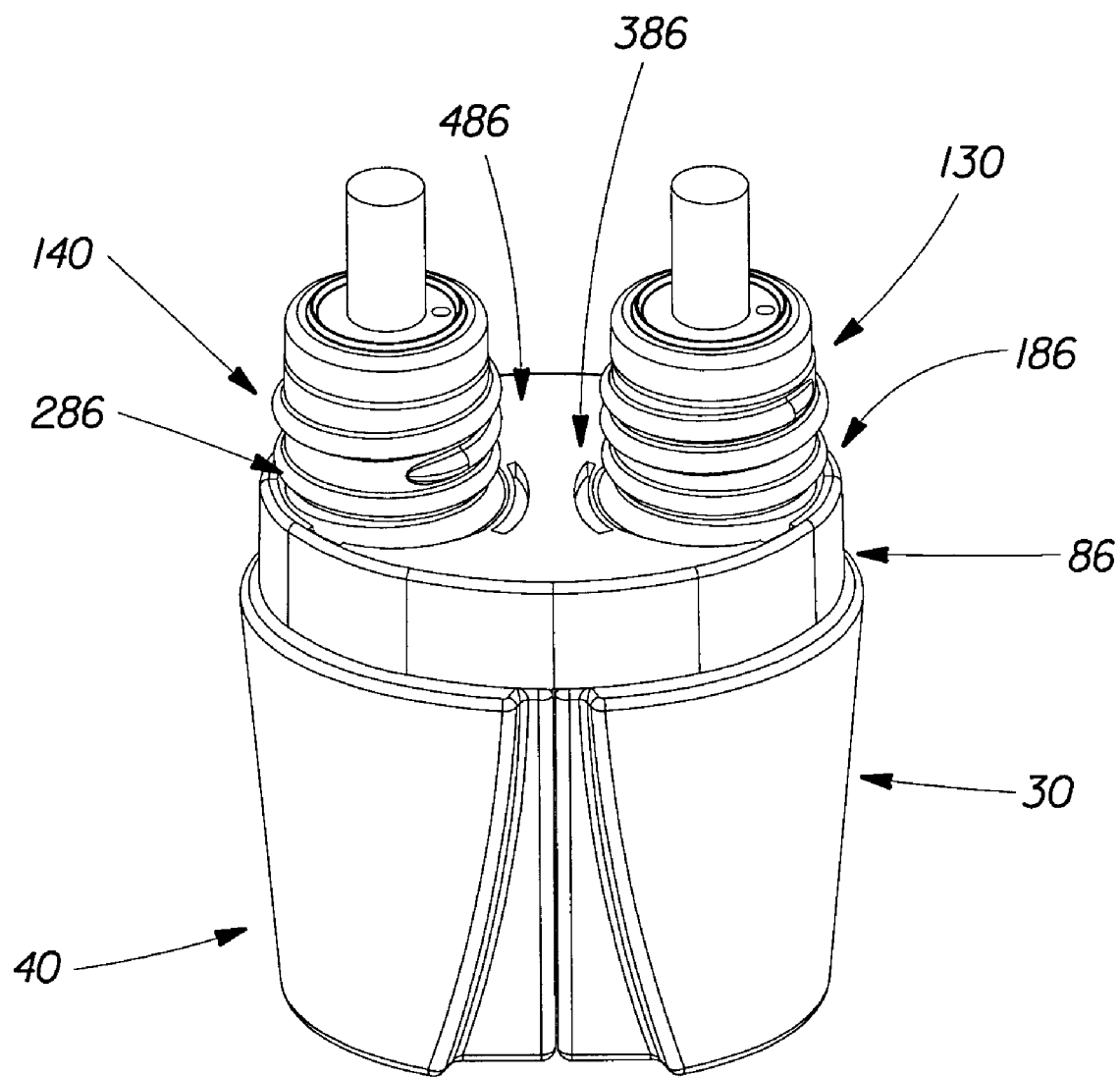
FIG. 8 is a perspective view of a cartridge according to another embodiment of the invention.

In yet another embodiment shown in FIG. 8, a first container 30 and at least a second container 40 can be operably connected to a retaining member 86 having an opening 186 which can be engaged by the neck 130 of the container 30 and a second opening 286 which can be engaged by the neck 140 of the second containers 40. In one embodiment, the retaining member 86 includes a first slit 386 and a second slit 486 which can be engaged by either the first or second protrusions 1170 or 1270 of the clip members 170, 270. One skilled in the art will understand that in this embodiment, the retaining member 84 allows a user to connect containers, which do not include the projections previously discussed, to a vaporizing unit.

Figure 9:
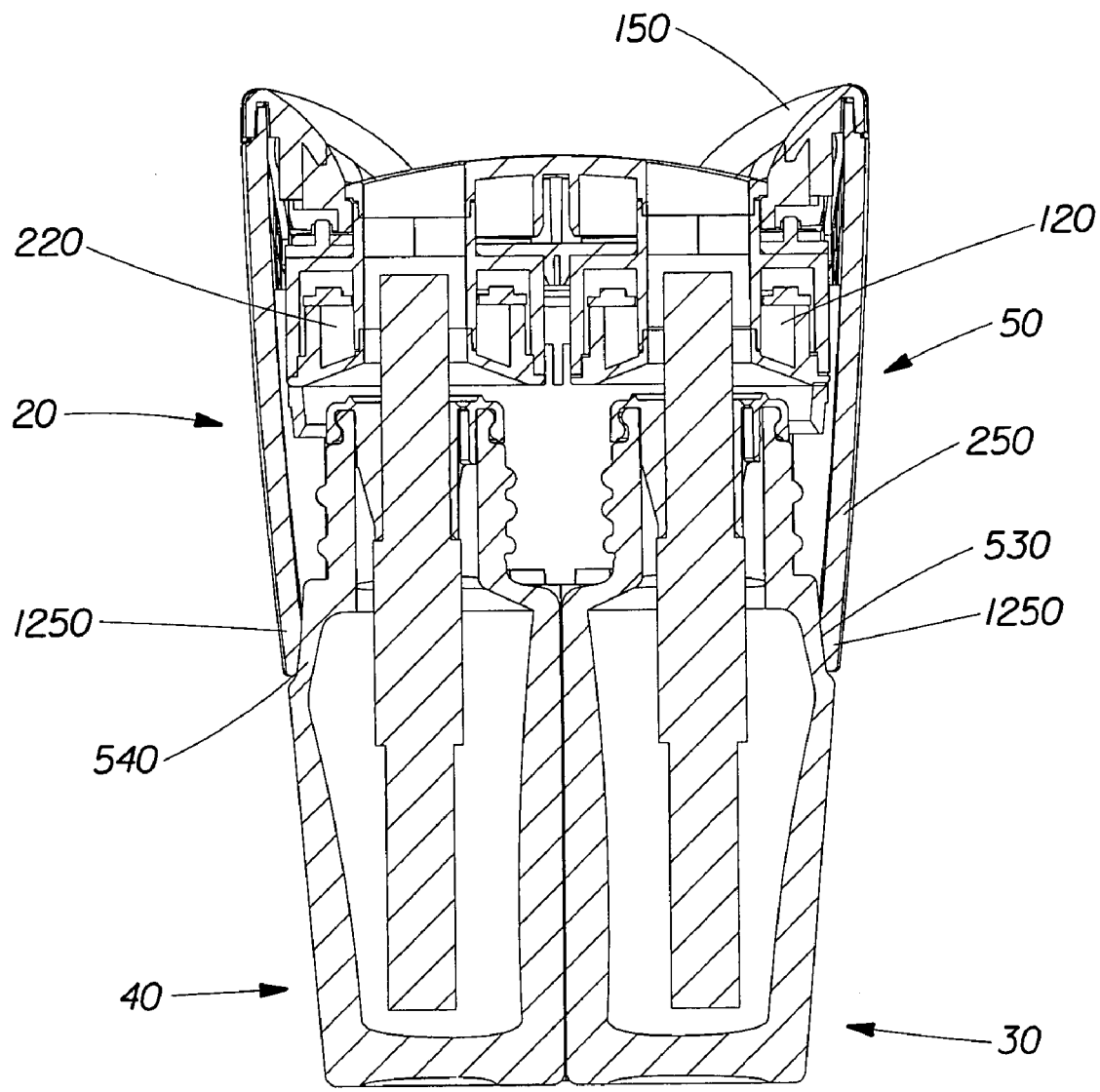
FIG. 9 is a cross-sectional view of containers connected to a vaporizing unit according to one embodiment of the invention.

FIG. 9 shows a cross-sectional view of the vaporizing unit 20 and a first and second container 30 and 40 inserted within the semi-enclosed cavity formed by the lower portion 250 of the housing 50 in order to be operably connected to the vaporizing unit. In this embodiment, the first and second containers 30, 40 are dimensioned such that when both containers are inserted in the semi-enclosed cavity, a portion 530 and 540 of each container is frictionally contacting at least respective portions 1250 of the inner surface of the bottom housing 250. In this embodiment, the friction generated between the containers and the bottom housing 250 is enough to hold the containers in place during use and can be easily overcome by a user when he or she desires to remove the containers from the vaporizing unit.

Figure 10:
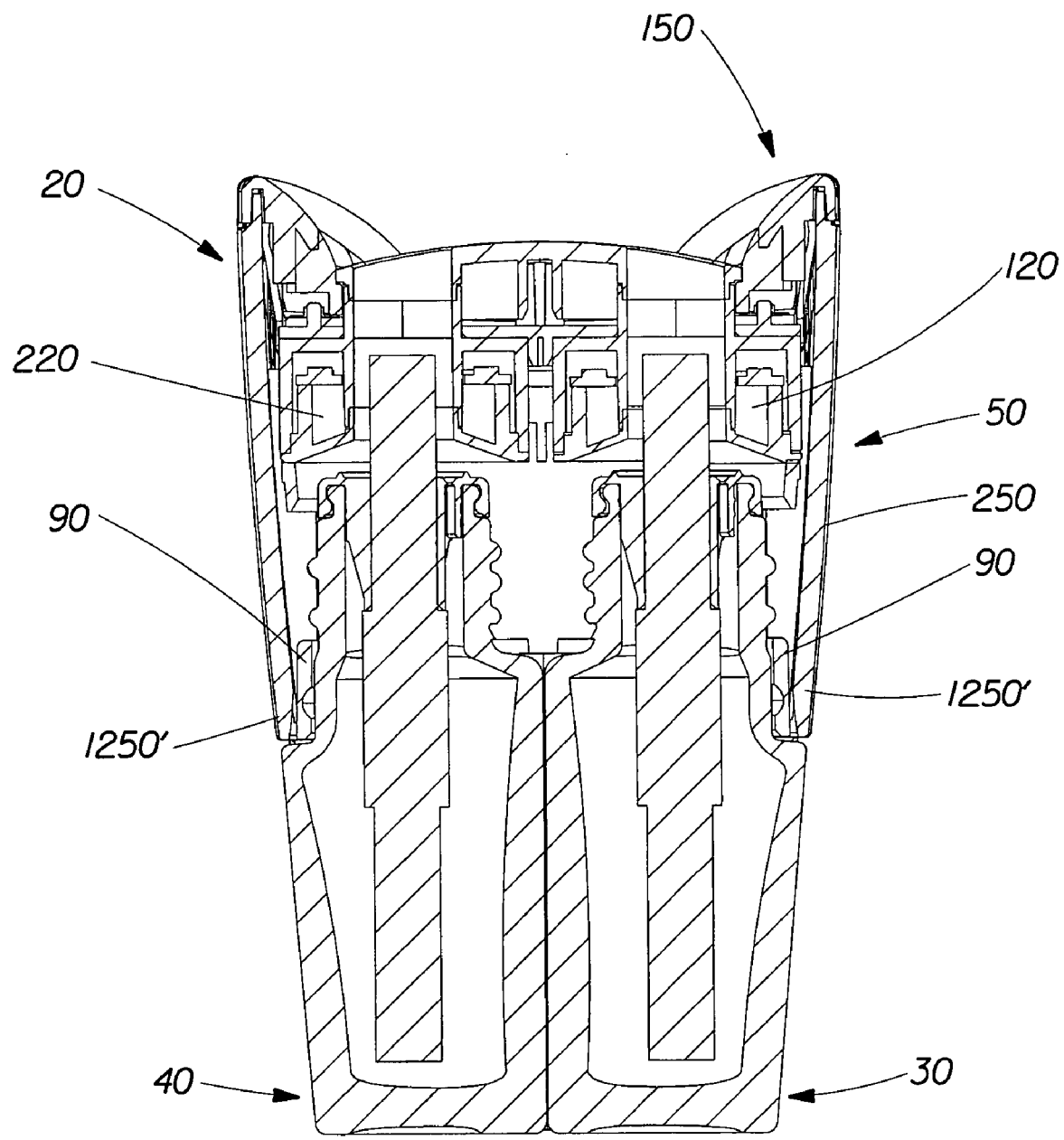
FIG. 10 is a cross-sectional view of containers connected to a vaporizing unit according to another embodiment of the invention.
Figure 11:
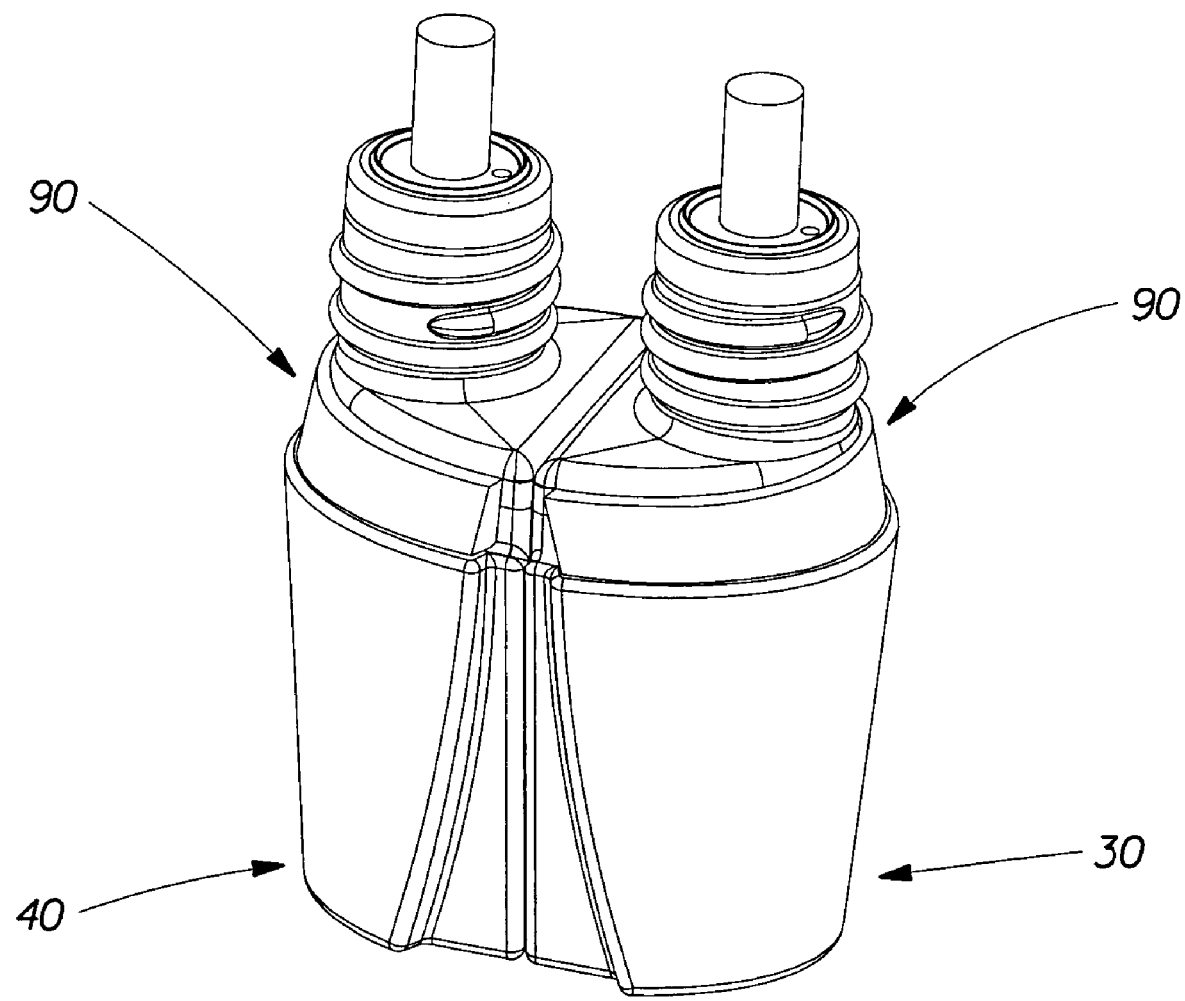
FIG. 11 is a perspective view of the cartridge shown in FIG. 10.

FIG. 10 shows a cross-sectional view of the vaporizing unit 20 and a first and second container 30 and 40 inserted within the semi-enclosed cavity formed by the lower portion 250 of the housing 50 and maintained in place by an adhesive. In this embodiment, at least a portion 530' and 540' is coated with an adhesive 90 for contacting and releasably adhering to at least respective portions 1250' of the bottom housing 250. The adhesive can be any adhesive known in the art allowing the containers to be held in place during use and also allowing a user to remove the containers when he or she desires. Non-limiting examples of suitable adhesive include pressure sensitive adhesives, hotmelts and tacky polymers. The adhesive can be applied to form one or more dots or to form a continuous strip around the portion of each container which can be in facial relationship with the bottom housing as shown in FIG. 11. In one embodiment, the first and second containers having an adhesive as previously discussed can in addition be operably connected to each other to form a cartridge such that they can be substantially concurrently connected to the vaporizing unit. In another embodiment, the first and second containers are separate and can be connected to the vaporizing unit separately.

It can be appreciated that when the first and/or second containers are dimensioned to provide a friction fit with the housing or when they include an adhesive, the vaporizing unit does not need to include a separate holding mechanism.

Figure 12:
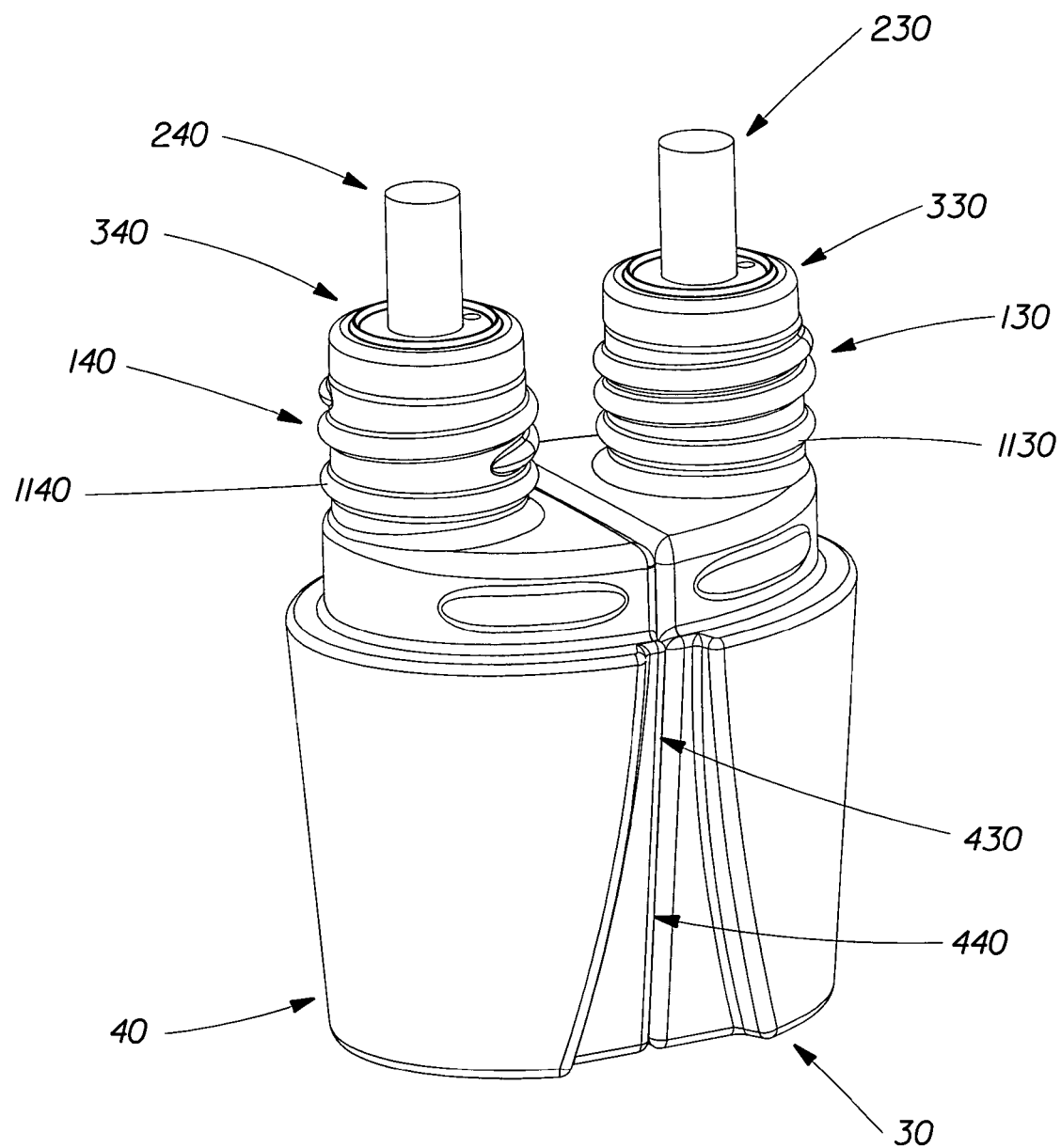
FIG. 12 is a perspective view of a cartridge according to another embodiment of the invention.

In one embodiment shown in FIG. 12, the first container 30 can be operably connected to the second container 40 by an adhesive. In a preferred embodiment, a facial side 430 of the first container can be adhesively connected to a corresponding facial side 440 of the second container.

One skilled in the art will understand that other mechanisms for operably connecting the first container to the second container can be used and still provide the same benefits. Non-limiting examples of suitable mechanisms include hook and loop fasteners, rubber band, a shrink-wrap film or sleeve, stretched film or sleeve or adhesive tape positioned around both the first and second containers.

When the first container is operably connected to the second container as previously discussed, a user can then releasably connect the containers 30 and 40 or a cartridge formed by the first and second containers to the vaporizing unit 20.

Figure 13:
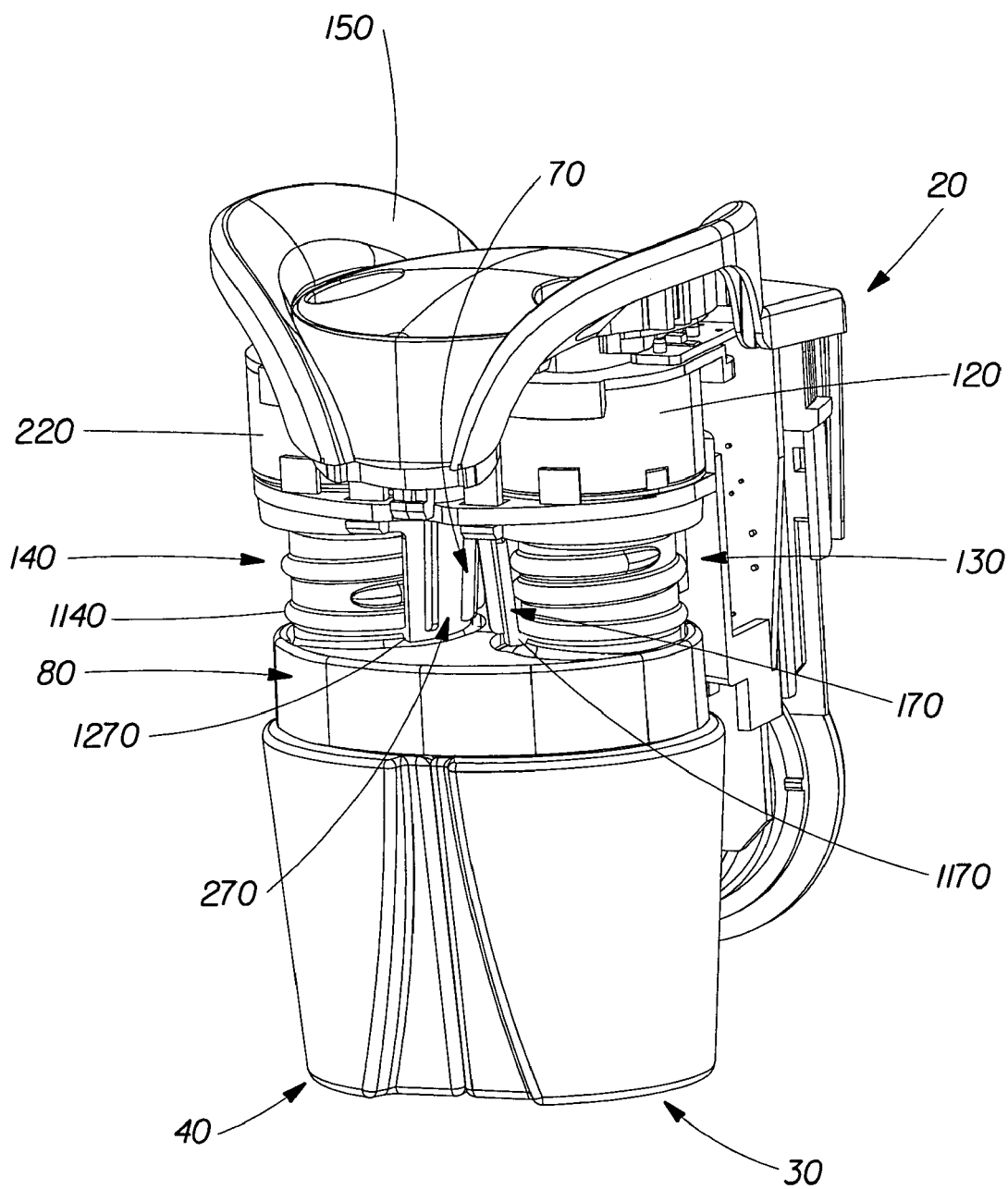
FIG. 13 is a perspective view of the cartridge of FIG. 5 that is operably connected to the vaporizing unit of FIG. 2.

A user can connect the containers 30 and 40 to the vaporizing unit 20 by inserting the top portion of the containers within the semi-enclosed cavity formed by the lower housing until the projections 1130 and 1140 engage and are moved past the protrusions 1170 and 1270 of the flexible first and second clip members 170 and 270 as shown in FIG. 13. When the projections 1130 and 1140 are moved past the protrusions 1170 and 1270, the containers 30 and 40 are held in place.

When the containers are connected to the vaporizing unit 20, the first and second wicks are located in the vicinity of the inner surface of respectively the first and second heating elements of the unit. A user can then start the device in order to vaporize the first and second volatile compositions either substantially concurrently or sequentially. Alternatively, a user can connect the containers while the vaporizing device is already plugged to an electrical outlet or simply powered by batteries.

In order to remove and/or replace the containers, a user can very simply pull on the containers.

One skilled in the art will understand that the projections 1130 and 1140 of the first and second containers and the protrusions 1170 and 1270 of the first and second clip members are similar to a tongue and groove mechanism. It will be appreciated that other combinations are possible and still provide the same benefits. For example, the projections 1130 and 1140 can engage corresponding recesses formed on the clip members 170 and 270. Alternatively, the protrusions 1170 and 1270 can engage recesses respectively formed on the neck 170 and 270 of the containers and still provide the same benefits.

It will be also appreciated that the previous device can include alternatively more than two heating elements and two containers.

Figure 14:
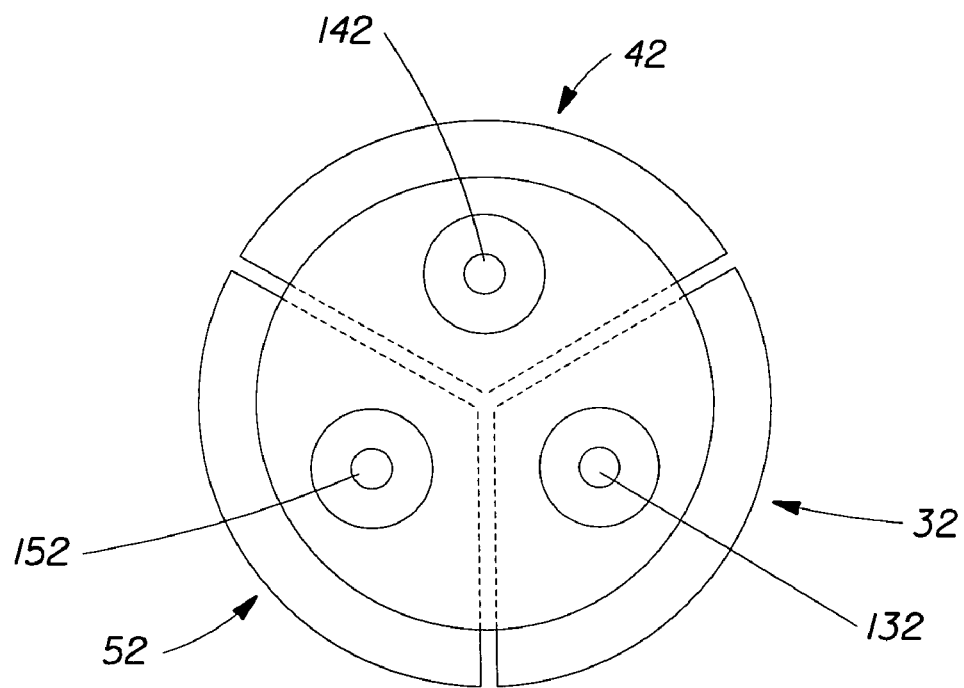
FIG. 14 is a schematical top view of a cartridge having three containers.

FIG. 14 shows a top view of three containers 32, 42 and 52 having corresponding wicks 132, 142 and 152 which are operably connected and which can store a first, a second and a third volatile composition.

Figure 15:
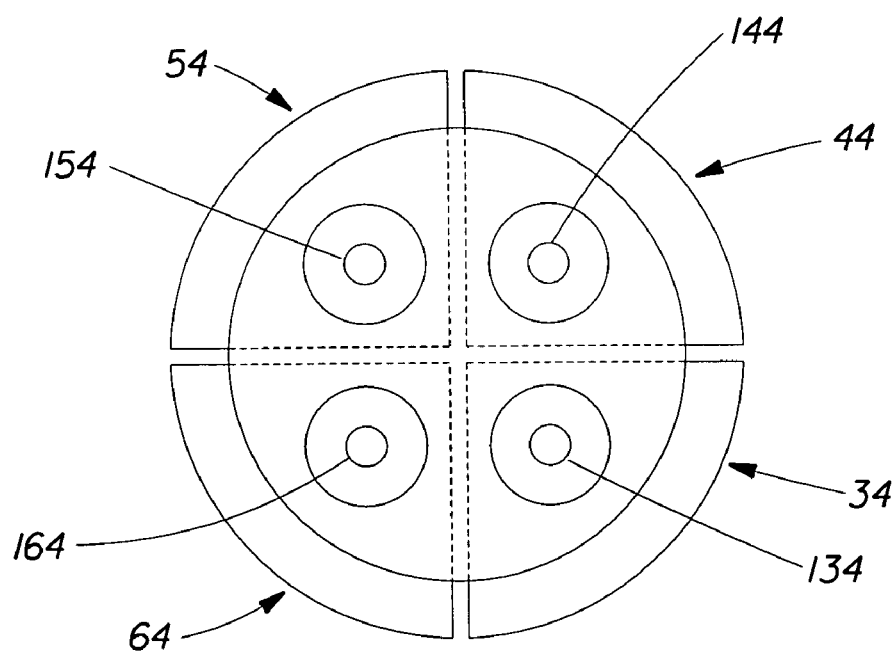
FIG. 15 is a schematical top view of a cartridge having four containers.

FIG. 15 shows a top view of four containers 34, 44, 54 and 64 having corresponding wicks 134, 144, 154 and 164 which are also operably connected and which can store, a first, a second, a third and a fourth volatile composition.

One skilled in the art will understand that it can be preferred that each container includes its own wick and that the vaporizing unit includes a corresponding number of heating elements.

Figure 16:
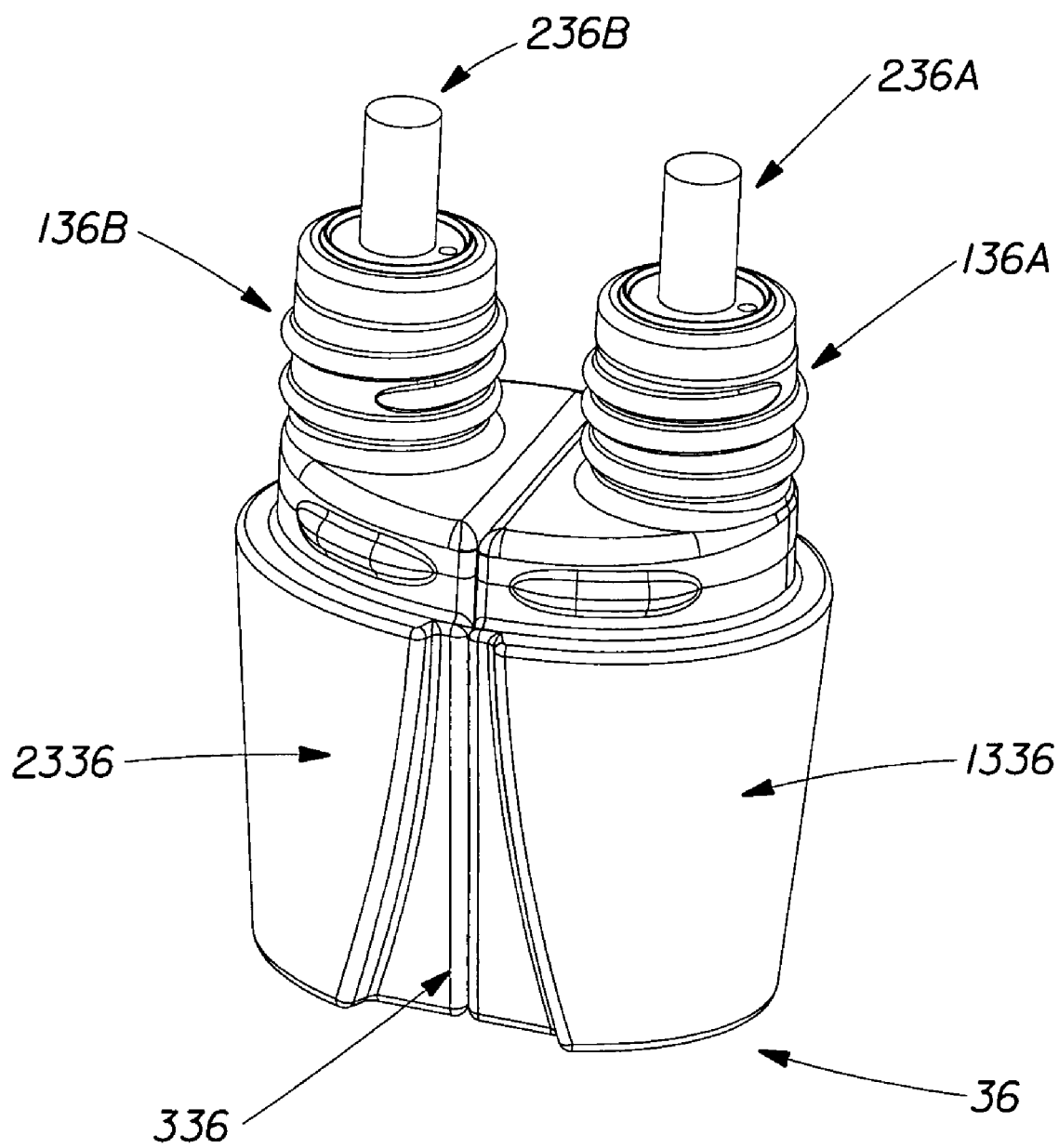
FIG. 16 is a perspective view of a single container according to another embodiment of the invention.

In one embodiment shown in FIG. 16, a single container 36 can include a first and second neck 136A and 136B, a first and a second wick 236A and 236B for delivering a first and a second volatile composition.

In this embodiment, the container preferably include and inner wall 336 separating the container into a first and a second volume or chamber 1336 and 2336 and preventing the first and second volatile compositions from mixing together.

In one embodiment, a first and a second container can be operably connected to a vaporizing unit without requiring the first and second containers to be operably connected to each other independently from the vaporizing unit prior to their insertion in the semi-enclosed cavity. In this embodiment, the first and second containers are preferably dimensioned such that at least portions of the first and second containers are in contact with corresponding portions of the inner surface of the lower housing forming the semi-enclosed cavity. In this embodiment, the frictional force generated by the first and second clip members 170 and 270 of the holding mechanism onto the containers is enough to maintain the first and second containers connected to the vaporizing unit.

In one embodiment, a first container is inserted within the semi-enclosed cavity and then a second container is also inserted within the remaining available space of the semi-enclosed cavity.

In one embodiment, a user can rotate the vaporizing unit such that the lower opening of the semi-enclosed cavity faces substantially upwards. A user can then insert the first and at least second containers either substantially concurrently or independently from each other.

The containers previously described can be made of any material know in the art such as for example glass, plastic and/or metal.

In one embodiment, the containers previously described can be sold individually with instructions in the form of words and/or pictures explaining to the consumer how to operably connect at least two containers together in order to connect the containers to the vaporizing unit.

In one embodiment, at least two containers can be sold already operably connected to each other.

In one embodiment, the neck portion of the containers previously described can include threads for receiving a cap.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:

1. A device for emitting at least two volatile compositions, said device comprising:
   (a) a vaporizing unit comprising:
      (i) a first heating element;
      (ii) at least a second heating element; and
      (iii) a holding mechanism;
   (b) a cartridge comprising:
      (i) a first container comprising a first volatile composition;
      (ii) a second container comprising a second volatile composition; and
      (iii) a retaining member for operably connecting said first container and said second container independently of said holding mechanism, said retaining member defining a first opening for receiving and releasably engaging said first container and a second opening for receiving and releasably engaging said second container,
   wherein said cartridge is releasably connected to said vaporizing unit by said holding mechanism.

2. The device of claim 1 wherein said holding mechanism is located substantially in between said first and second heating elements.

3. The device of claim 1 wherein said vaporizing unit comprises a housing forming a semi-enclosed cavity for receiving at least a portion of said first and second containers.

4. The device of claim 3 wherein said holding mechanism comprises a first and at least a second flexible clip member extending substantially downwardly within at least a portion of said semi-enclosed cavity.

5. The device of claim 4 wherein said first flexible clip member comprises a first protrusion extending outwardly and said second flexible clip member comprises a second protrusion extending outwardly wherein said first and second protrusions extend towards substantially opposite directions.

6. The device of claim 1 wherein said first and second volatile compositions comprise distinct perfumes.

7. The device of claim 1 wherein said first volatile composition is substantially the same as said second volatile composition.

8. The device of claim 1 wherein said holding mechanism comprises a first clip element, and wherein said retaining member comprises a first clip member extending upwardly from a top surface of said retaining member, wherein said first clip element engages said first clip member.

9. A cartridge for a device for emitting at least a first and a second volatile composition, said cartridge comprising:
(a) a first container defining a first volume and comprising a first neck extending from the top portion of said first container and a first wick in communication with said first volume, said first wick extending at least partially through an opening of said first container, wherein said first volume comprises a first volatile composition; and
(b) at least a second container defining a second volume and comprising a second neck extending from the top portion of said second container and a second wick in communication with said second volume, said second wick extending at least partially through an opening of said second container, wherein said second volume comprises a second volatile composition; and
(c) a retaining member for operably connecting said first container and said second container independently of a holding mechanism, said retaining member defining a first opening for receiving and releasably engaging said first neck of said first container and a second opening for receiving and releasably engaging said second neck of said second container,
wherein said first wick is fixedly located relative to said second wick when said first container is operably connected to said second container.

10. The cartridge of claim 9 wherein said first container is adhesively connected to said second container.

11. The cartridge of claim 9 wherein said first container comprises a first neck and said second container comprises a second neck.

12. The cartridge of claim 11 wherein said first neck comprises a first projection and said second neck comprises a second projection.

13. A method of emitting a first and at least a second volatile composition with a vaporizing unit capable of vaporizing a first and at least a second volatile composition, said method comprising:
(a) providing a cartridge comprising:
  (i) a first container comprising a first neck extending from the top portion of said first container and a first volatile composition contained in said first container;
  (ii) a second container comprising a second neck extending from the top portion of said second container and a second volatile composition container in said second container; and
  (iii) a retaining member for operably connecting said first container and said second container independently of a holding mechanism, said retaining member defining a first opening for receiving and releasably engaging said first neck of said first container and a second opening for receiving and releasably engaging said second neck of said second container;
(b) operably connecting said first container to said second container;
(c) operably and substantially concurrently connecting said cartridge to said vaporizing unit; and
(d) actuating said vaporizing unit.

14. The method of claim 13 wherein said first container comprises a first wick in communication with said first volatile composition and said second container comprises a second wick in communication with said second volatile composition.

15. The method of claim 13 wherein said first volatile composition and said second volatile composition comprise distinct perfumes.

16. The method of claim 13 wherein said first volatile composition is substantially the same as said second volatile composition.

17. A cartridge for a vaporizing unit capable of emitting a first and at least a second volatile composition, said cartridge comprising:
(a) a first container comprising a first neck extending from the top portion of said first container and a first volatile composition contained in said first container;
(b) a second container comprising a second neck extending from the top portion of said second container and a second volatile composition contained in said second container;
(c) a first wick in communication with said first volatile composition and extending at least partially outside of said first volume;
(d) a second wick in communication with said second volatile composition and extending at least partially outside of said second volume; and
(e) a retaining member for operably connecting said first container and said second container independently of a holding mechanism, said retaining member defining a first opening for receiving and releasably engaging said first neck of said first container and a second opening for receiving and releasably engaging said second neck of said second container, said retaining member comprising a first clip member extending upwardly from a top surface of said retaining member
wherein said first wick is fixedly located relative to said second wick when said first container is operably connected to said second container.

18. The cartridge of claim 17 wherein said first volatile composition and said second volatile compositions comprise distinct perfumes.

19. The cartridge of claim 17 wherein said first volatile composition is substantially the same as said second volatile composition.

20. The cartridge of claim 17 wherein said first clip member is adjacent said second opening.

21. The cartridge of claim 17 wherein said retaining member further comprises a second clip member extending from a top surface of said retaining member and wherein said second clip member is substantially adjacent to said first container.

22. A device for emitting at least two volatile compositions, said device comprising:
(a) a vaporizing unit comprising:
  (i) a first heating element;
  (ii) at least a second heating element;
  (iii) a holding mechanism comprising a first and a second flexible clip member, said first and second flexible clip members extend substantially downwardly, wherein said first flexible clip member comprises a first protrusion extending outwardly and said second flexible clip member comprises a second protrusion extending outwardly, wherein said first and second protrusions extend towards substantially opposite directions;
(b) a cartridge comprising:
  (i) a first container comprising a first volatile composition and a first neck portion having a first projection;
  (ii) a second container comprising a second volatile composition and a second neck portion having a second projection;
  (iii) a retaining member for operably connecting said first container and said second container independently of said holding mechanism, said retaining member defining a first opening for receiving and releasably engaging said first container and a second opening for receiving and releasably engaging said second container;
wherein said first protrusion releasably engages said first projection of said first neck portion and said second protrusion releasably engages said second projection of said second neck portion.

* * * * *